(12) United States Patent
Hasegawa et al.

(10) Patent No.: US 10,576,215 B2
(45) Date of Patent: Mar. 3, 2020

(54) PRE-FILLED SYRINGE

(71) Applicant: NIPRO CORPORATION, Osaka-shi, Osaka (JP)

(72) Inventors: Mitsuru Hasegawa, Osaka (JP); Minoru Honda, Osaka (JP)

(73) Assignee: NIPRO CORPORATION, Osaka-Shi (JP)

( * ) Notice: Subject to any disclaimer, the term of this patent is extended or adjusted under 35 U.S.C. 154(b) by 84 days.

(21) Appl. No.: 15/039,776

(22) PCT Filed: Nov. 5, 2014

(86) PCT No.: PCT/JP2014/079299
§ 371 (c)(1),
(2) Date: May 26, 2016

(87) PCT Pub. No.: WO2015/079874
PCT Pub. Date: Jun. 4, 2015

(65) Prior Publication Data
US 2017/0000954 A1 Jan. 5, 2017

(30) Foreign Application Priority Data

Nov. 27, 2013 (JP) ................................ 2013-244820

(51) Int. Cl.
*A61M 5/315* (2006.01)
*A61M 5/28* (2006.01)
(Continued)

(52) U.S. Cl.
CPC .......... *A61M 5/31596* (2013.01); *A61M 5/19* (2013.01); *A61M 5/284* (2013.01);
(Continued)

(58) Field of Classification Search
CPC ................... A61M 5/19; A61M 5/284; A61M 2005/3132; A61M 5/31501;
(Continued)

(56) References Cited

U.S. PATENT DOCUMENTS

| | | | |
|---|---|---|---|
| 5,605,542 A | * | 2/1997 | Tanaka .................. A61M 5/284 604/86 |
| 5,788,670 A | | 8/1998 | Reinhard et al. |

(Continued)

FOREIGN PATENT DOCUMENTS

| | | |
|---|---|---|
| CN | 1080874 A | 1/1994 |
| CN | 1694745 A | 11/2005 |

(Continued)

OTHER PUBLICATIONS

Extended European Search Report dated May 23, 2017 for European Application No. 14866233.1.

(Continued)

*Primary Examiner* — Shefali D Patel
(74) *Attorney, Agent, or Firm* — Birch, Stewart, Kolasch & Birch, LLP

(57) ABSTRACT

A pre-filled syringe includes: a cylindrical container, a front end-side gasket; a rear end-side gasket; an intermediate gasket partitioning an inside of the cylindrical container into a front chamber and a rear chamber; a plunger; a medical drug contained in the front chamber, and a liquid drug contained in the rear chamber. In a state where the plunger is pushed in, a bypass portion included in the cylindrical container faces a groove portion provided in the intermediate gasket, thereby allowing communication between the front chamber and the rear chamber therethrough, so that the medical drug and the liquid drug are mixed, and a liquid mixture is discharged. The pre-filled syringe further includes a movement limiting mechanism for limiting movement of (Continued)

the plunger such that a tail end of the rear end-side gasket does not reach the bypass portion.

4 Claims, 15 Drawing Sheets

(51) Int. Cl.
    *A61M 5/19*       (2006.01)
    *A61M 5/31*       (2006.01)
    *A61M 5/32*       (2006.01)

(52) U.S. Cl.
    CPC .... *A61M 5/31501* (2013.01); *A61M 5/31505* (2013.01); *A61M 5/31513* (2013.01); *A61M 5/3202* (2013.01); *A61M 2005/3131* (2013.01); *A61M 2005/3132* (2013.01); *A61M 2005/31508* (2013.01)

(58) Field of Classification Search
    CPC .... A61M 5/31505; A61M 2005/31506; A61M 2005/31508; A61M 5/31596; A61M 2005/31598
    See application file for complete search history.

(56) References Cited

U.S. PATENT DOCUMENTS

| | | |
|---|---|---|
| 6,582,407 B1 | 6/2003 | Lo |
| 7,699,811 B2 * | 4/2010 | Hasegawa ............ A61M 5/3134 604/122 |
| 2004/0064105 A1 * | 4/2004 | Capes .................... A61M 5/348 604/218 |
| 2007/0161961 A1 | 7/2007 | Hasegawa |
| 2008/0234632 A1 | 9/2008 | Hasegawa |
| 2013/0090596 A1 | 4/2013 | Asai et al. |

FOREIGN PATENT DOCUMENTS

| | | |
|---|---|---|
| CN | 1933862 A | 3/2007 |
| CN | 102958551 A | 3/2013 |
| DE | 4445969 C1 | 3/1996 |
| EP | 0568321 A2 | 11/1993 |
| EP | 0793973 A2 | 9/1997 |
| JP | 6-7446 A | 1/1994 |
| JP | 2003-205034 A | 7/2003 |
| JP | 2006-500161 A | 1/2006 |
| JP | 2007-185319 A | 7/2007 |

OTHER PUBLICATIONS

Chinese Office Action and Search Report, dated Nov. 2, 2018 for Chinese Application No. 201480064567.3, with English translations.

\* cited by examiner

FIG.8
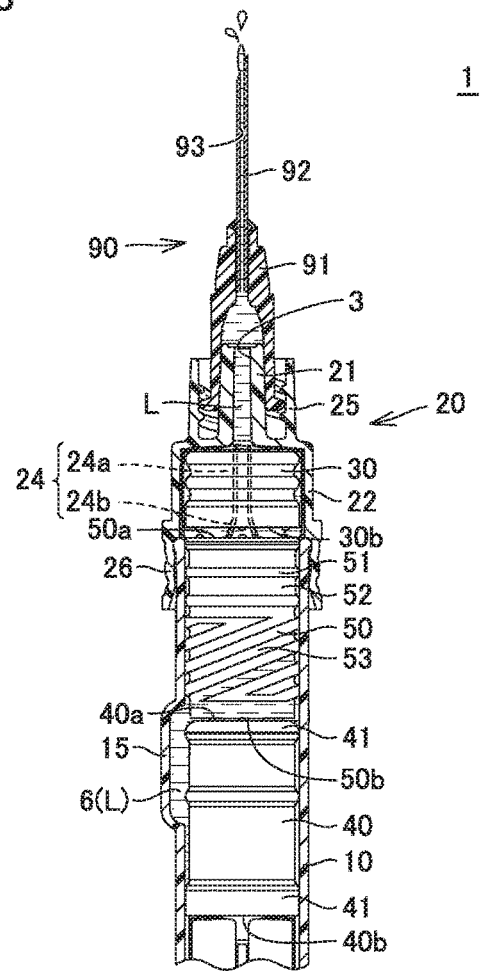
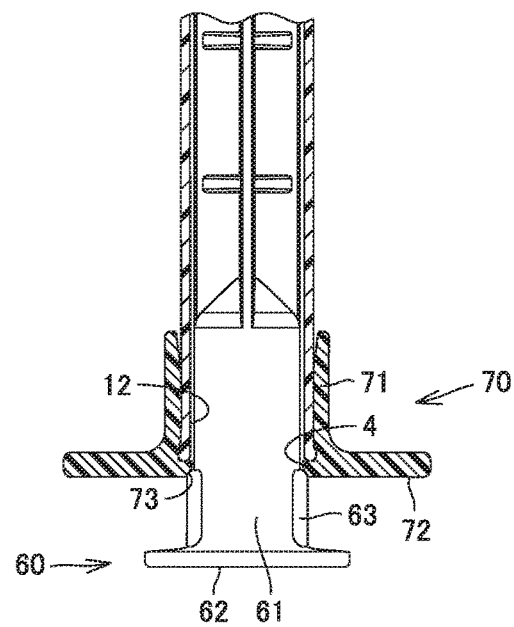

FIG.10
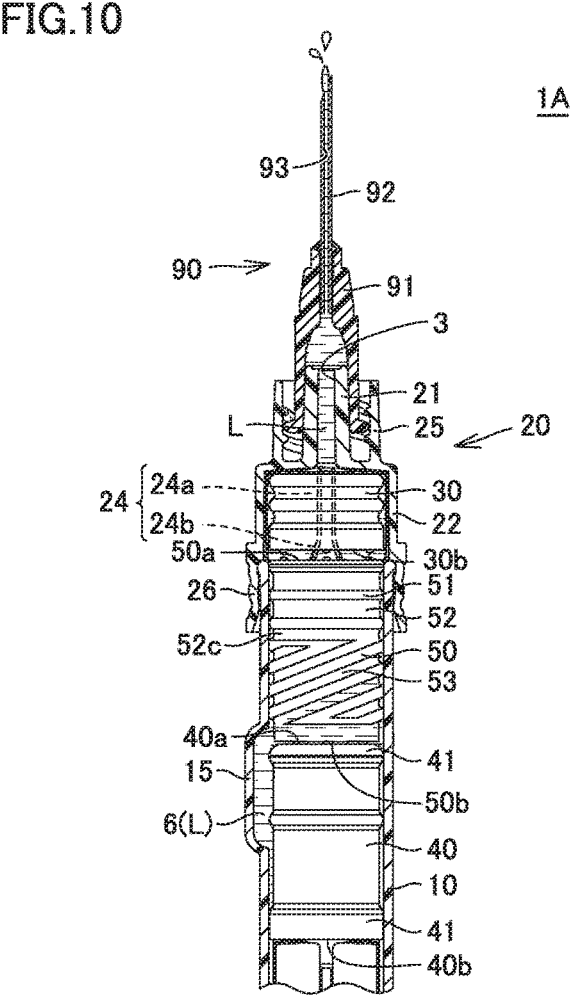
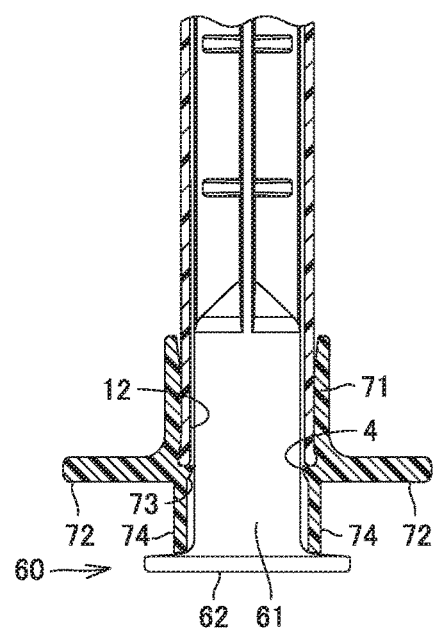

FIG.12
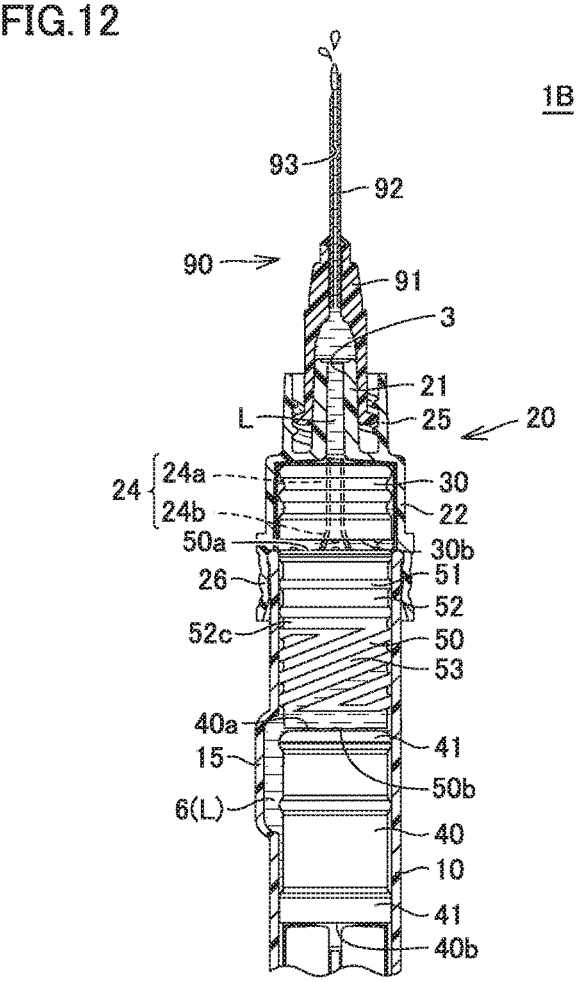
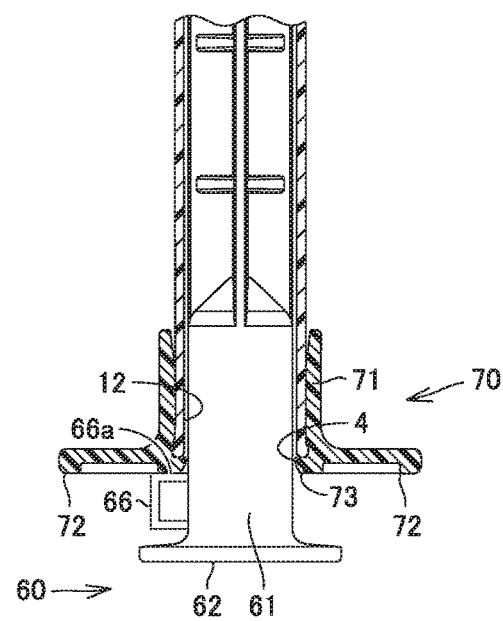

FIG.15
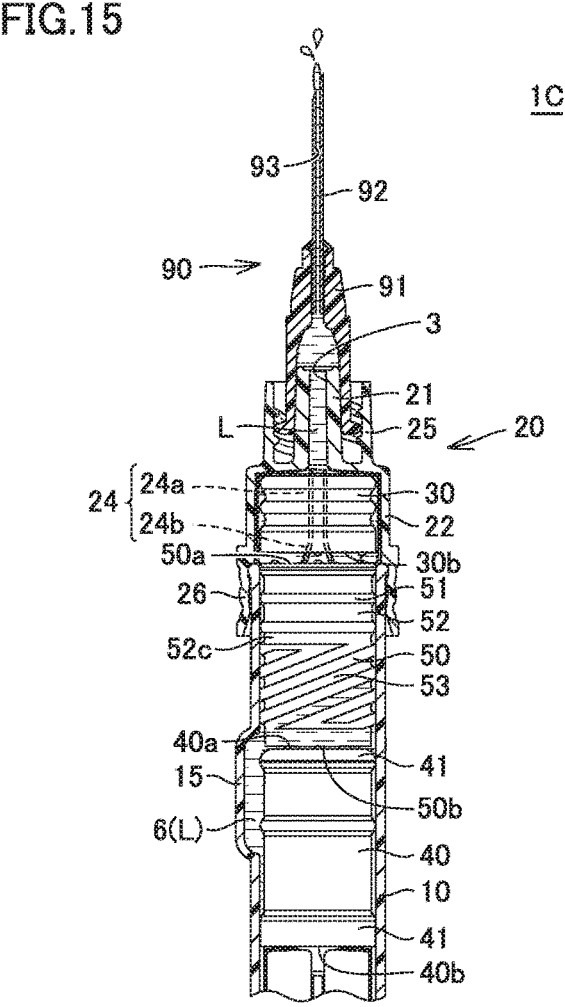
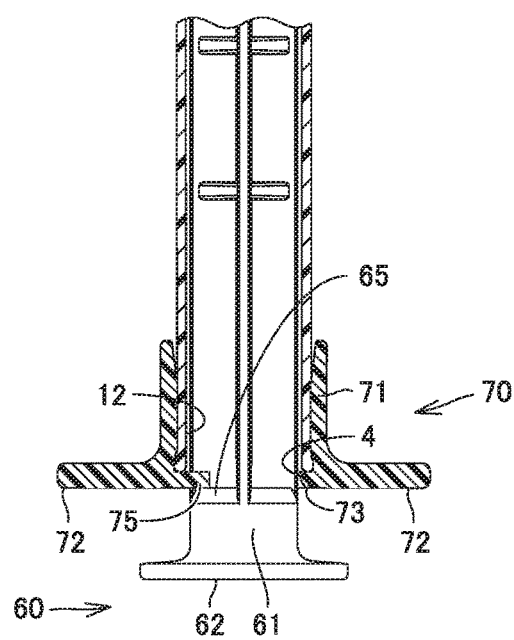

PRE-FILLED SYRINGE

CROSS-REFERENCE TO RELATED APPLICATIONS

This application is the National Phase of PCT International Application No. PCT/JP2014/079299, filed on Nov. 5, 2014, which claims priority under 35 U.S.C. § 119(a) to Patent Application No. 2013-244820, filed in Japan on Nov. 27, 2013.

TECHNICAL FIELD

The present invention relates to a pre-filled syringe, and particularly to a pre-filled syringe for mixing a medical drug and a liquid drug inside a cylindrical container partitioned by a gasket, and discharging the mixture to the outside.

BACKGROUND ART

In recent years, a pre-filled syringe has been developed: functioning as a container capable of containing a medical drug and a liquid drug in advance required for medical treatments by ensuring stability during storage of the medical drug and the liquid drug; and also functioning an injection syringe during use.

For example, Japanese Patent Laying-Open No. 2007-185319 (PTD 1) discloses such a pre-filled syringe.

The pre-filled syringe disclosed in PTD 1 includes: a cylindrical portion having a front end and a rear end that are opened; a nozzle portion attached to the front end of the cylindrical portion and having a discharge path; a front end-side gasket, an intermediate gasket and a rear end-side gasket provided on the front end side, the intermediate portion and the rear end side, respectively, of the cylindrical portion so as to freely slide inside the cylindrical portion; and a plunger capable of pushing the rear end-side gasket toward the front end. A medical drug is contained in a front chamber provided inside the cylindrical portion and located between the front end-side gasket and the intermediate gasket. A liquid drug is contained in a rear chamber provided inside the cylindrical portion and located between the intermediate gasket and the rear end-side gasket.

In the state where the plunger is not pushed in, the nozzle portion and the front chamber are maintained in a liquid-tight state by the front end-side gasket; the front chamber and the rear chamber are maintained in a liquid-tight state by the intermediate gasket; and the rear chamber is maintained in a liquid-tight state also by the rear end-side gasket.

The cylindrical portion is provided with a bypass portion bulging in its radial direction, and the intermediate gasket has an outer circumferential surface provided with a groove portion. In the state where the bypass portion and the groove portion face each other, the front chamber and the rear chamber are brought into communication with each other.

Furthermore, the nozzle portion has a housing portion capable of housing the front end-side gasket on the side at which this nozzle portion is attached to the cylindrical portion. When the front end-side gasket moves to the housing portion, the discharge path and the front chamber are brought into communication with each other through a space provided between the circumferential surface of the front end-side gasket and the nozzle portion.

When the plunger is pushed toward the front end of the cylindrical portion, the front end-side gasket, the intermediate gasket and the rear end-side gasket move toward the front end. In this case, the front end-side gasket moves to the nozzle portion, thereby allowing communication between the discharge path and the front chamber, and also causing the groove portion of the intermediate gasket and the bypass portion of the cylindrical portion to face each other, so that the front chamber and the rear chamber communicate with each other through the groove portion and the bypass portion.

In the state where the front chamber and the rear chamber communicate with each other, a liquid drug is pushed forward by the rear end-side gasket, so that the liquid drug contained in the rear chamber is moved to the front chamber and mixed with the medical drug, thereby preparing a liquid mixture. By further pushing the plunger in the state where the liquid mixture is prepared, the intermediate gasket pushed into the rear end-side gasket moves toward the front end, so that the liquid mixture is pushed into the nozzle portion by the intermediate gasket. Thereby, the liquid mixture is discharged through the discharge path to the outside.

CITATION LIST

Patent Document

PTD 1: Japanese Patent Laying-Open No. 2007-185319

SUMMARY OF INVENTION

Technical Problem

In PTD 1, however, the level of user's power for pushing the plunger may vary. Thus, in the case where the plunger is excessively pushed in, the tail end of the rear end-side gasket may be pushed forward beyond the bypass portion.

In such a case, it becomes difficult to maintain the rear chamber in a liquid-tight state by the rear end-side gasket. Accordingly, the liquid mixture and the liquid drug remaining in the rear chamber or the bypass portion are to flow backward through the bypass portion. This consequently causes liquid leakage, in which a liquid mixture and a liquid drug leak from the rear end of the cylindrical portion.

Since a highly toxic liquid drug may be used as a liquid drug used for medical treatments, it is necessary to prevent liquid leakage for preventing adhesion of such a toxic liquid drug to the user.

The present invention has been made in light of the above-described problems. An object of the present invention is to provide a pre-filled syringe capable of preventing liquid leakage resulting from excessive pushing of the plunger.

Solution to Problem

A pre-filled syringe according to the present invention includes: a cylindrical container having a front end provided with a discharge path and a rear end provided with an opening; a front end-side gasket provided at a position closer to the front end of the cylindrical container so as to partition a space inside the cylindrical container, the front end-side gasket being freely slidable inside the cylindrical container; a rear end-side gasket provided at a position closer to the rear end of the cylindrical container so as to partition the space inside the cylindrical container, the rear end-side gasket being freely slidable inside the cylindrical container; an intermediate gasket provided inside the cylindrical container so as to partition, into a front chamber and a rear chamber, a portion of the space inside the cylindrical container that is located between the front end-side gasket and the rear end-side gasket, the intermediate gasket being freely slidable inside the cylindrical container; a plunger, a part of which being inserted through the opening into the cylindrical container such that the plunger is connected to the rear end-side gasket, thereby allowing the rear end-side gasket to be pushed toward the front end of the cylindrical container; a medical drug contained in the front chamber; and a liquid drug contained in the rear chamber.

The cylindrical container has a bypass portion protruding in a radially outward direction. The intermediate gasket has an outer circumferential surface provided with a groove portion that faces the bypass portion in a state where the intermediate gasket is disposed to face the bypass portion. In a state where the plunger is not pushed in, the bypass portion faces the front chamber and does not face the groove portion, thereby allowing the front chamber and the rear chamber to be maintained in a liquid-tight state by the intermediate gasket, and the front chamber does not communicate with the discharge path, thereby allowing the front chamber and the discharge path to be maintained in a liquid-tight state by the front end-side gasket.

In a state where the plunger is pushed in, the rear end-side gasket, the intermediate gasket and the front end-side gasket move toward the front end of the cylindrical container, to cause the bypass portion to face the groove portion, thereby allowing communication between the front chamber and the rear chamber through the bypass portion and the groove portion, to mix the medical drug and the liquid drug so as to prepare a liquid mixture, and allowing communication between the front chamber and the discharge path, to cause the liquid mixture to be discharged through the discharge path to outside. The pre-filled syringe according to the present invention described above further includes a movement limiting mechanism for limiting movement of the plunger such that a tail end of the rear end-side gasket located closer to the plunger is prevented from reaching the bypass portion in the state where the plunger is pushed in.

In the pre-filled syringe according to the present invention described above, it is preferable that the plunger includes a rod portion connected to the rear end-side gasket and extending in an axial direction of the cylindrical container such that a part of the rod portion is located outside the cylindrical container. Furthermore, it is preferable that the rod portion has a protruding portion protruding in a radially outward direction and located outside the cylindrical container in a state where the plunger is not pushed in. In this case, it is preferable that the movement limiting mechanism is formed of the protruding portion and the cylindrical container. It is preferable that, in the state where the plunger is pushed in, the protruding portion comes in contact with the cylindrical container, thereby limiting movement of the plunger.

In the pre-filled syringe according to the present invention described above, it is preferable that the plunger includes: a rod portion connected to the rear end-side gasket and extending in an axial direction of the cylindrical container such that a part of the rod portion is located outside the cylindrical container; and a diameter increasing portion provided at a rear end of the rod portion. Furthermore, it is preferable that the cylindrical container has the rear end provided with a protruding portion that protrudes toward outside in the axial direction of the cylindrical container. In this case, it is preferable that the movement limiting mechanism is formed of the diameter increasing portion and the protruding portion. It is preferable that, in the state where the plunger is pushed in, the diameter increasing portion comes in contact with the protruding portion, thereby limiting movement of the plunger.

In the pre-filled syringe according to the present invention described above, it is preferable that the cylindrical container includes: a cylindrical portion housing the front end-side gasket, the intermediate gasket and the rear end-side gasket in the state where the plunger is not pushed in; and a nozzle portion having the discharge path and attached to a front end of the cylindrical portion. Furthermore, it is preferable that the nozzle portion includes: a housing portion located adjacent to the front end of the cylindrical portion and being capable of housing the front end-side gasket in the state where the plunger is pushed in; and a discharge portion located closer to a front end of the nozzle portion and communicating with the housing portion. Furthermore, it is preferable that the discharge path is defined by the housing portion and the discharge portion. In this case, it is preferable that, in the state where the plunger is pushed in, the discharge portion and the front chamber communicate with each other through a space between the housing portion and a circumferential surface of the front end-side gasket moved from the cylindrical portion to the housing portion, thereby discharging the liquid mixture through the discharge path to outside. It is preferable that, when the plunger is pushed in, the front end-side gasket is pushed in by the intermediate gasket, thereby limiting movement of the plunger at a position where the nozzle portion does not fall off from the cylindrical portion.

Advantageous Effects of Invention

According to the present invention, a pre-filled syringe capable of preventing liquid leakage resulting from excessive pushing of a plunger can be provided.

BRIEF DESCRIPTION OF DRAWINGS

FIG. 4 is a diagram showing the positional relationship between a bypass portion of a cylindrical portion and an intermediate gasket in the state where a plunger is not pushed in.

FIG. 8 is a schematic cross-sectional view showing the state where the liquid mixture is discharged from the pre-filled syringe.

FIG. 10 is a schematic cross-sectional view showing the state where a liquid mixture is discharged from the pre-filled syringe shown in FIG. 9.

FIG. 12 is a schematic cross-sectional view showing the state where a liquid mixture is discharged from the pre-filled syringe shown in FIG. 11.

FIG. 15 is a schematic cross-sectional view showing the state where a liquid mixture is discharged from the pre-filled syringe shown in FIG. 13.

DESCRIPTION OF EMBODIMENTS

Figure 1:
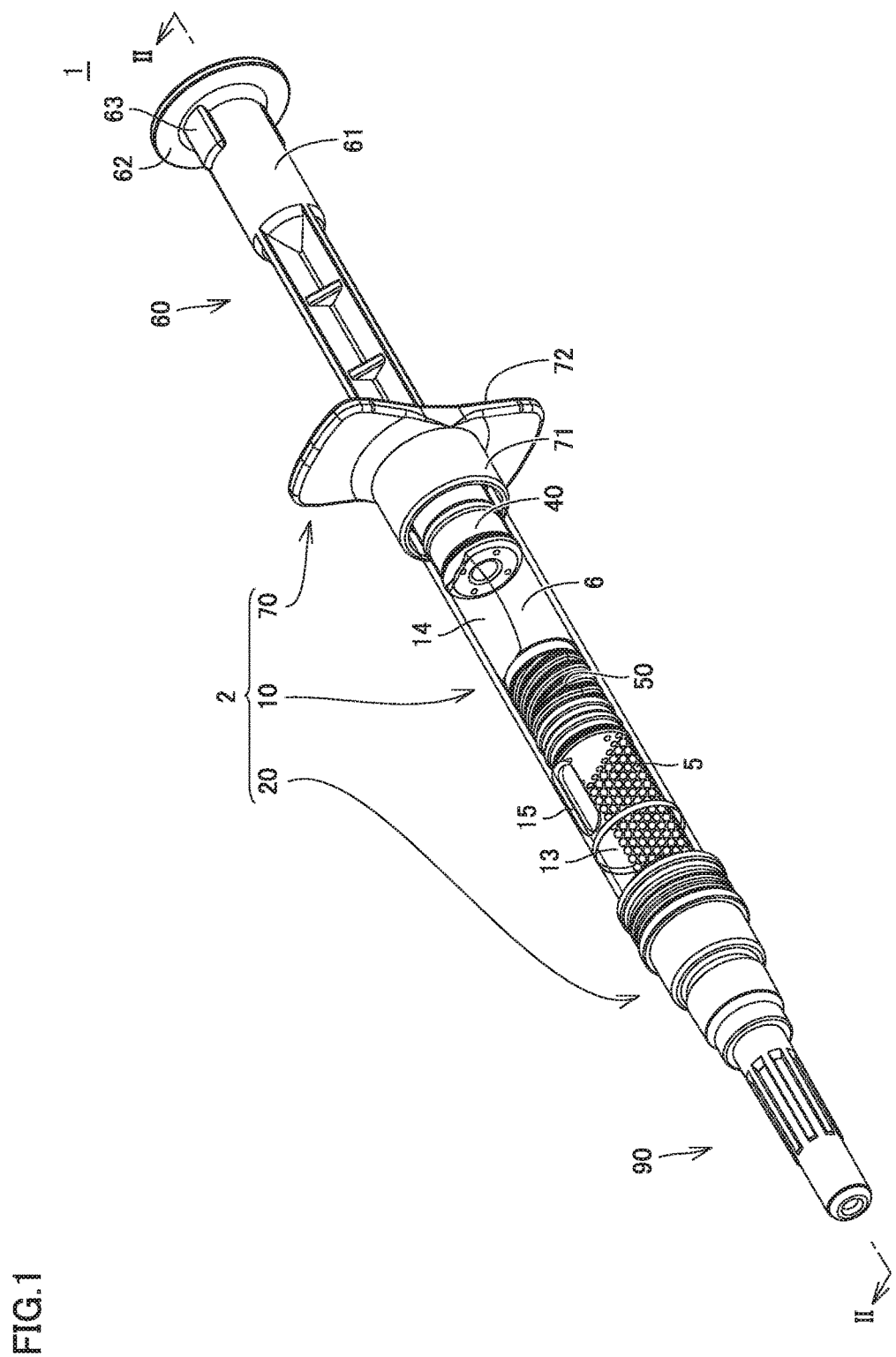
FIG. 1 is an external view of a pre-filled syringe according to the first embodiment of the present invention.

Embodiments of the present invention will be hereinafter described in detail with reference to the accompanying drawings. In the embodiments described below, the same or corresponding components are designated by the same reference characters, and description thereof will not be repeated.

First Embodiment

Figure 2:
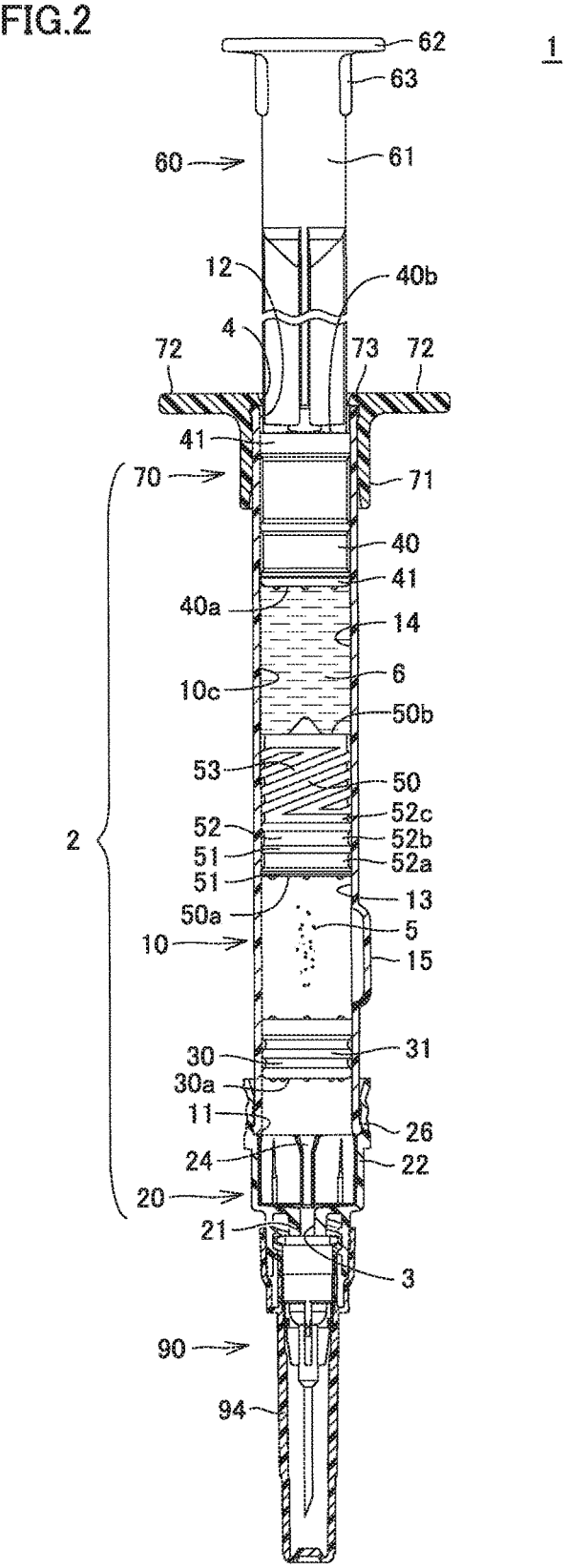
FIG. 2 is a schematic cross-sectional view taken along a line II-II shown in FIG. 1.
Figure 3:
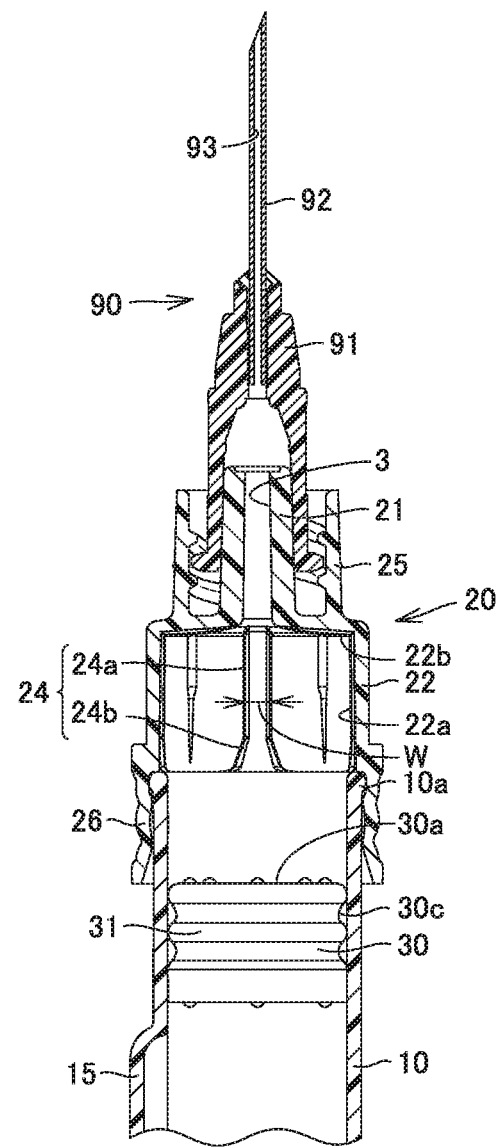
FIG. 3 is a schematic cross-sectional view showing details of a nozzle portion shown in FIG. 1.

FIG. 1 is an external view of a pre-filled syringe according to the present embodiment. FIG. 2 is a schematic cross-sectional view taken along a line II-II shown in FIG. 1. FIG. 3 is a schematic cross-sectional view showing details of a nozzle portion shown in FIG. 1. Referring to FIGS. 1 to 3, a pre-filled syringe 1 according to the present embodiment will be hereinafter described. FIGS. 1 to 3 each show the state where a plunger 60 provided in pre-filled syringe 1 is not pushed in.

As shown in FIGS. 1 and 2, pre-filled syringe 1 according to the present embodiment includes: a cylindrical container 2 having a front end provided with a discharge path 3 and a rear end provided with an opening 4; a front end-side gasket 30; a rear end-side gasket 40; an intermediate gasket 50; and a plunger 60.

Cylindrical container 2 includes: a cylindrical portion 10 having a fore end provided with an opening 11 and a base end provided with an opening 12; a nozzle portion 20 attached at the fore end of cylindrical portion 10; and a flange portion 70 provided at the base end of cylindrical portion 10. Nozzle portion 20 has a front end equipped with an injection needle unit 90.

In the state where plunger 60 is not pushed in, cylindrical portion 10 houses front end-side gasket 30, intermediate gasket 50 and rear end-side gasket 40 sequentially from the fore end side. Inside cylindrical portion 10, a front chamber 13 is formed between front end-side gasket 30 and intermediate gasket 50 while a rear chamber 14 is formed between intermediate gasket 50 and rear end-side gasket 40. Front chamber 13 contains a medical drug 5 while rear chamber 14 contains a liquid drug 6. Furthermore, cylindrical portion 10 has a bypass portion 15 provided so as to partially bulge in its radial direction.

Materials for forming cylindrical portion 10 may, for example, be glass, polyolefin resin such as polyethylene and polypropylene, polyvinyl chloride, PET (polyethylene terephthalate), EVA (ethylene vinyl acetate copolymer), EVOH (ethylene-vinylalcohol copolymer), polyamide, polyvinylidene chloride, polyvinyl fluoride, poly trifluorochloroethylene, polyester, nylon, a mixture thereof, and a stacked body thereof, but raw materials thereof are not particularly limited as long as they have been actually used as medical device materials and may not interact with the liquid drug contained in cylindrical portion 10 and not elute to the liquid drug.

Examples of medical drug 5 contained in front chamber 13 may desirably be a freeze-dried formulation such as antibiotics, but the dosage form of medical drug 5 contained in front chamber 13 is not particularly limited, and a liquid medical drug that should be mixed immediately before use may be employed. Liquid drug 6 contained in rear chamber 14 may desirably be solutions such as a physiological saline solution and a dextrose solution or a medical solution.

As shown in FIGS. 2 and 3, nozzle portion 20 includes a discharge portion 21, a housing portion 22, and an attachment portion 26. Nozzle portion 20 is liquid-tightly attached to the fore end of cylindrical portion 10 via attachment portion 26 located at the rear end of this nozzle portion 20. Furthermore, nozzle portion 20 has a discharge path 3.

Discharge portion 21 is located at the front end of nozzle portion 20. Discharge portion 21 is configured so as to be capable of discharging a liquid mixture L (see FIG. 7) prepared by mixing medical drug 5 and liquid drug 6. Also, discharge portion 21 is provided so as to communicate with housing portion 22.

In the state where nozzle portion 20 is attached to cylindrical portion 10, housing portion 22 is located adjacent to a fore end 10a of cylindrical portion 10. Housing portion 22 is provided so as to be capable of housing front end-side gasket 30 in the state where plunger 60 is pushed in. Housing portion 22 has a flow passage portion 24 through which liquid mixture L can be moved to discharge portion 21 in the state where front end-side gasket 30 is housed.

Flow passage portion 24 is a concave groove provided in each of an inner circumferential surface 22a and a bottom surface 22b of housing portion 22. Flow passage portion 24 has a narrow-width portion 24a and a wide-width portion 24b in a portion provided in inner circumferential surface 22a of housing portion 22. Narrow-width portion 24a extends approximately linearly in the axial direction of cylindrical container 2. Wide-width portion 24b has a width greater than a width W of narrow-width portion 24a and is inclined such that its width increases toward the rear.

Flow passage portion 24 is disposed so as to face a front end 30a and a circumferential surface 30c of front end-side gasket 30 in the state where front end-side gasket 30 is housed in housing portion 22. In this case, a space is provided between flow passage portion 24 and front end-side gasket 30. Liquid mixture L moves through this space from housing portion 22 to discharge portion 21. In this way, discharge path 3 of nozzle portion 20 is defined by discharge portion 21 and housing portion 22 communicating therewith.

Furthermore, nozzle portion 20 includes an insertion portion 25 through which injection needle unit 90 is inserted. Injection needle unit 90 includes a puncture needle 92, a base body 91 connected to puncture needle 92, and a protector 94. Base body 91 is slightly opened at its fore end side so as to be capable of communicating with a hollow passage 93 of puncture needle 92, and opened at its rear end side so as to be inserted into discharge portion 21 in a sealed manner. Thereby, in the state where injection needle unit 90 is inserted into insertion portion 25, hollow passage 93 and discharge portion 21 communicate with each other. In addition, puncture needle 92 is protected by protector 94 until before use of pre-filled syringe 1.

Materials for forming nozzle portion 20 may, for example, be polyolefin resin such as polyethylene and polypropylene, polyvinyl chloride, PET (polyethylene terephthalate), EVA (ethylene vinyl acetate copolymer), EVOH (ethylene-vinyl-alcohol copolymer), polyamide, polyvinylidene chloride, polyvinyl fluoride, poly trifluorochloroethylene, polyester, nylon, a mixture thereof, and a stacked body thereof, but raw materials thereof are not particularly limited as long as they have been actually used as medical device materials and may not interact with the liquid drug contained in cylindrical portion 10 and not elute to the liquid drug.

As shown in FIGS. 1 and 2, front end-side gasket 30 is provided at a position closer to the front end of cylindrical container 2 so as to partition the space inside cylindrical container 2, and configured so as to be freely slidable inside cylindrical container 2. Front end-side gasket 30 has an annular rib 31. Annular rib 31 presses inner circumferential surface 10*c* of cylindrical portion 10 across the entire region in the circumferential direction, so that front end-side gasket 30 maintains discharge path 3 and front chamber 13 in a liquid-tight state.

Rear end-side gasket 40 is provided at a position closer to the rear end of cylindrical container 2 so as to partition the space inside cylindrical container 2, and configured so as to be freely slidable inside cylindrical container 2. Rear end-side gasket 40 has a fore end 40*a* and a tail end 40*b* each provided with an annular rib 41. Annular rib 41 presses inner circumferential surface 10*c* of cylindrical portion 10 across the entire region in the circumferential direction, so that rear end-side gasket 40 maintains rear chamber 14 in a liquid-tight state. Furthermore, tail end 40*b* of rear end-side gasket 40 is connected to plunger 60.

Intermediate gasket 50 is provided inside cylindrical container 2 so as to partition, into front chamber 13 and rear chamber 14, a portion of the space inside cylindrical container 2 that is located between front end-side gasket 30 and rear end-side gasket 40. Intermediate gasket 50 is also configured so as to be freely slidable inside cylindrical container 2. Intermediate gasket 50 has an outer circumferential surface provided with: a plurality of annular groove portions 52 (52*a*, 52*b*, 52*c*) formed in the circumferential direction; annular ribs 51 provided between the plurality of annular groove portions 52 and at fore end 50*a* of the intermediate gasket; and a spiral groove portion 53 formed in a spiral shape.

Annular rib 51 presses inner circumferential surface 10*c* of cylindrical portion 10 across the entire region in the circumferential direction, so that intermediate gasket 50 maintains front chamber 13 and rear chamber 14 in a liquid-tight state.

Annular groove portion 52*c* of the plurality of annular groove portions 52 that is located closer to rear end 50*b* is continuous to spiral groove portion 53. Thereby, when plunger 60 is pushed in to thereby move intermediate gasket 50 so that annular groove portion 52*c* and bypass portion 15 face each other, front chamber 13 and rear chamber 14 are brought into communication with each other through spiral groove portion 53, annular groove portion 52*c* and bypass portion 15.

Materials for forming front end-side gasket 30, intermediate gasket 50 and rear end-side gasket 40 may, for example, be suitably elastic materials such as butyl rubber, silicone rubber, a thermoplastic elastomer, and a silicone elastomer, but raw materials thereof are not particularly limited as long as they have been actually used as medical device materials and do not interact with the liquid drug contained in cylindrical portion 10.

Plunger 60 is configured to be partially inserted through opening 4 of cylindrical container 2 into cylindrical container 2 and thereby connected to rear end-side gasket 40, so that rear end-side gasket 40 can be pushed toward the front end of cylindrical container 2.

Plunger 60 includes a rod portion 61 and a diameter increasing portion 62. Rod portion 61 is connected to rear end-side gasket 40 and extends in the axial direction of cylindrical container 2 such that a part of this rod portion 61 is located outside cylindrical container 2. Diameter increasing portion 62 is provided at the rear end of rod portion 61. Diameter increasing portion 62 is larger in radial dimension than rod portion 61.

Rod portion 61 includes a protruding portion 63 protruding in a radially outward direction and located outside cylindrical container 2 in the state where plunger 60 is not pushed in. For example, protruding portion 63 is provided in the vicinity of the rear end of rod portion 61.

Materials for forming plunger 60 maybe a synthetic resin and the like, but raw materials thereof are not particularly limited.

Flange portion 70 includes a cylindrical portion 71, and a flange portion 72 and an engagement portion 73. Cylindrical portion 71 is configured such that it can be fitted on the outer circumferential surface of cylindrical portion 10. Flange portion 72 extends from the base end of cylindrical portion 71 in its radially outward direction. Engagement portion 73 is formed of an annular protruding ridge portion protruding from the base end of cylindrical portion 71 in its radially inward direction. Flange portion 70 is fixed to cylindrical portion 10 by fitting engagement portion 73 on the outer circumferential surface of cylindrical portion 10 such that this engagement portion 73 comes in contact with the base end of cylindrical portion 10.

Materials for forming flange portion 70 may be synthetic resin and the like, but raw materials thereof are not particularly limited.

Figure 4:
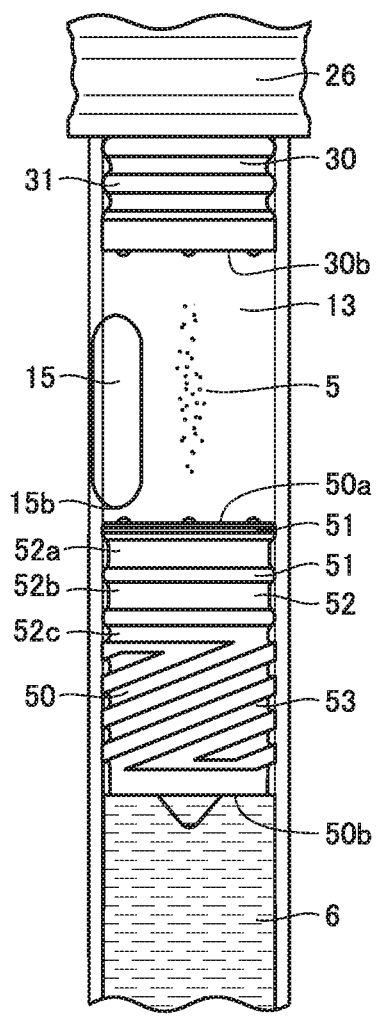
Figure 5:
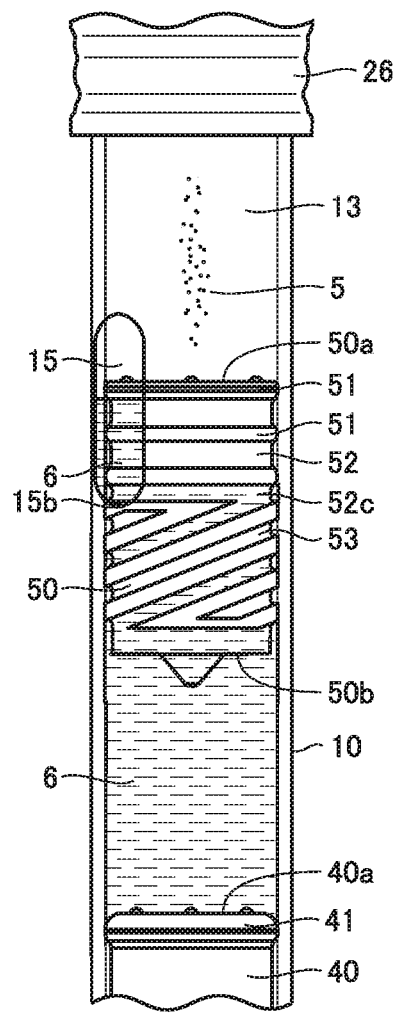
FIG. 5 is a diagram showing the state where the bypass portion and a groove portion of the intermediate gasket face each other.
Figure 6:
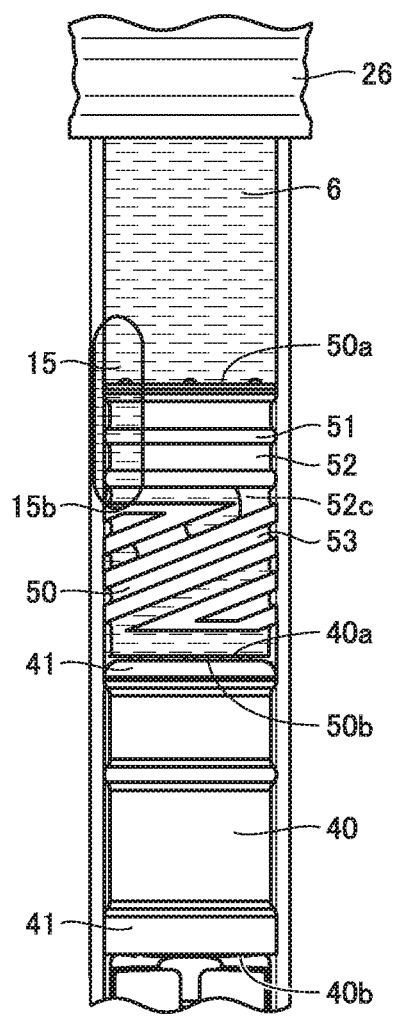
FIG. 6 is a diagram showing the state where a liquid drug moves from a rear chamber to a front chamber through the bypass portion and the groove portion of the intermediate gasket.
Figure 7:
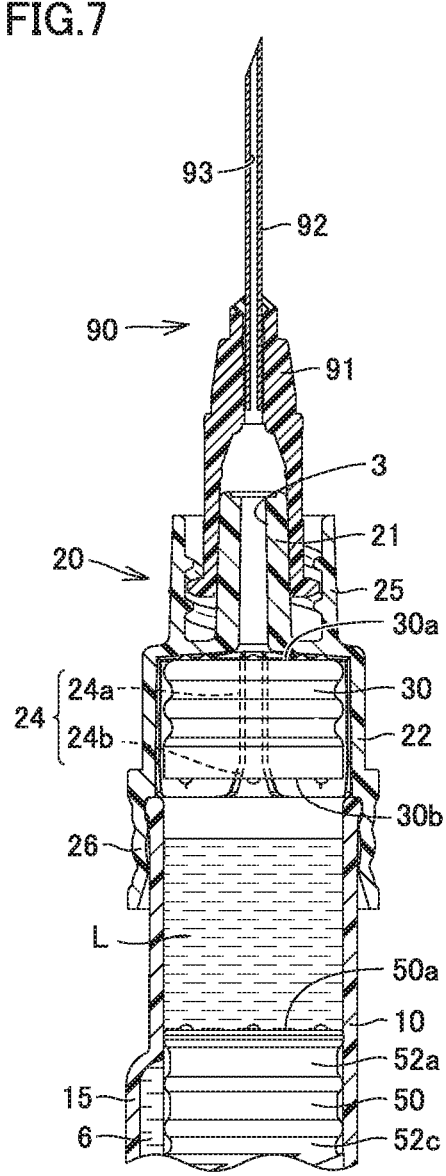
FIG. 7 is a diagram showing the positional relationship between a front end-side gasket and the intermediate gasket at the time when a medical drug and a liquid drug are mixed together.

FIG. 4 is a diagram showing the positional relationship between the bypass portion of the cylindrical portion and the intermediate gasket in the state where the plunger is not pushed in. FIG. 5 is a diagram showing the state where the bypass portion and a groove portion of the intermediate gasket face each other. FIG. 6 is a diagram showing the state where a liquid drug moves from a rear chamber through the bypass portion and the groove portion of the intermediate gasket to a front chamber. FIG. 7 is a diagram showing the positional relationship between the front end-side gasket and the intermediate gasket at the time when a medical drug and a liquid drug are mixed together. Referring to FIGS. 4 to 7, an explanation will be hereinafter given with regard to the operation performed when plunger 60 is pushed in for preparing medical drug 5 and liquid drug 6.

When pre-filled syringe 1 is used, this pre-filled syringe 1 is supported such that its front end is directed upward while preventing plunger 60 from being pushed in. In this state, as shown in FIG. 4, rear end 30*b* of front end-side gasket 30 does not reach housing portion 22, but is located forward of bypass portion 15. Fore end 50*a* of intermediate gasket 50 is located rearward of bypass portion 15.

In this way, in the state where plunger 60 is not pushed in, bypass portion 15 faces front chamber 13 but does not face annular groove portion 52 of intermediate gasket 50, so that front chamber 13 and rear chamber 14 are maintained in a liquid-tight state by intermediate gasket 50. Furthermore, front chamber 13 does not communicate with discharge path 3, so that front chamber 13 and discharge path 3 are maintained in a liquid-tight state by front end-side gasket 30.

Then, an index finger and a middle finger are hooked on flange portion 70, and a thumb is used to push diameter increasing portion 62 of plunger 60 in, so that plunger 60 is pushed toward the front end of pre-filled syringe 1. In this case, rear end-side gasket 40 connected at the fore end of plunger 60 is pushed in, thereby raising the internal pressure in rear chamber 14. Accordingly, intermediate gasket 50 moves toward the front end of pre-filled syringe 1. Furthermore, intermediate gasket 50 moves to thereby also raise the internal pressure in front chamber 13, so that front end-side gasket 30 also moves toward the front end of pre-filled syringe 1.

Intermediate gasket 50 moves, and annular rib 51 provided at fore end 50a of this intermediate gasket 50 passes through rear end 15b of bypass portion 15, so that intermediate gasket 50 and bypass portion 15 face each other. Furthermore, when intermediate gasket 50 is pushed in, annular groove portion 52c reaches bypass portion 15. As shown in FIG. 5, in the state where annular groove portion 52c faces bypass portion 15, front chamber 13 and rear chamber 14 communicate with each other through bypass portion 15 and also through spiral groove portion 53 and annular groove portion 52c that are continuous to each other. Thereby, liquid drug 6 contained in rear chamber 14 flows through spiral groove portion 53, annular groove portion 52c and bypass portion 15 into front chamber 13.

The internal pressure in front chamber 13 further rises as liquid drug 6 flows thereinto. Then, front end-side gasket 30 is inserted into nozzle portion 20 and housed in housing portion 22. This allows communication between housing portion 22 and front chamber 13, thereby releasing the tightly-sealed state of front chamber 13 by front end-side gasket 30. Furthermore, in the state where front end-side gasket 30 is housed in housing portion 22, housing portion 22 communicates with nozzle portion 21 and the outside through flow passage portion 24 and also through a gap between housing portion 22 and front end-side gasket 30.

This allows communication between discharge path 3 and front chamber 13, so that rear end-side gasket 40 can be pushed toward intermediate gasket 50 while discharging air within front chamber 13 to the outside. Consequently, as shown in FIG. 6, fore end 40a of rear end-side gasket 40 is brought into contact with rear end 50b of intermediate gasket 50, and almost all of liquid drug 6 contained in rear chamber 14 can be moved to front chamber 13. It is to be noted that part of liquid drug 6 remains in bypass portion 15, annular groove portion 52 and spiral groove portion 53.

Then, as shown in FIG. 7, intermediate gasket 50 is moved to a prescribed position through rear end-side gasket 40. Specifically, intermediate gasket 50 is moved to such a position that its fore end 50a passes through the front end of bypass portion 15, and the liquid level of liquid drug 6 does not reach the fore end of cylindrical portion 10. Then, pre-filled syringe 1 is shaken by the force enough to allow dispersion of medical drug 5, thereby mixing medical drug 5 and liquid drug 6 together for preparing liquid mixture L.

After preparation of liquid mixture L, plunger 60 is pushed in to introduce liquid mixture L into hollow passage 93 of puncture needle 92. In this case, few air bubbles existing in liquid mixture L can be readily caught since wide-width portion 24b of flow passage portion 24 is inclined so as to be increased in width toward the rear. Furthermore, since narrow-width portion 24a that is less in width than wide-width portion 24b is provided on the top end side of wide-width portion 24b, the flow velocity of liquid mixture L is increased when this liquid mixture L is discharged through flow passage portion 24. Thereby, the air bubbles caught in wide-width portion 24b can be discharged to the outside ahead of liquid mixture L without accumulating therein.

FIG. 8 is a schematic cross-sectional view showing the state where the liquid mixture is discharged from the pre-filled syringe. Referring to FIG. 8, an explanation will be hereinafter given with regard to the operation performed when a liquid mixture is discharged from the pre-filled syringe.

As shown in FIG. 8, in the state where hollow passage 93 of puncture needle 92 is filled with liquid mixture L, puncture needle 92 is inserted into a patient's target site, and plunger 60 is slowly pushed in for injection. Fore end 50a of intermediate gasket 50 is brought into contact with rear end 30b of front end-side gasket 30, so that liquid mixture L is discharged from hollow passage 93 and injected into a patient. In this case, protruding portion 63 of plunger 60 comes in contact with flange portion 70 on the rear end side of cylindrical container 2. Thereby, front end-side gasket 30 is pushed in by intermediate gasket 50, thereby limiting movement of plunger 60 at the position where nozzle portion 20 does not fall off from cylindrical portion 10. Also, movement of plunger 60 is limited such that tail end 40b of rear end-side gasket 40 located closer to plunger 60 does not reach bypass portion 15.

In this way, in pre-filled syringe 1 according to the present embodiment, protruding portion 63 and flange portion 70 function as a movement limiting mechanism for limiting movement of plunger 60. Accordingly, when plunger 60 is pushed in, excessive load is not applied to front end-side gasket 30 through intermediate gasket 50. Thereby, front end-side gasket 30 can be suppressed from pushing nozzle portion 20 into the front end side. Consequently, nozzle portion 20 can be prevented from falling off from cylindrical portion 10.

Furthermore, since movement of plunger 60 is limited so as to prevent tail end 40b of rear end-side gasket 40 from reaching bypass portion 15, rear chamber 14 can be maintained in a liquid-tight state reliably by annular rib 41 located at tail end 40b. Thereby, it becomes possible to prevent liquid leakage in which liquid mixture L or liquid drug 6 remaining in bypass portion 15 and in annular groove portion 52 and spiral groove portion 53 of intermediate gasket 50 leaks from the rear end of cylindrical container 2.

Second Embodiment

Figure 9:
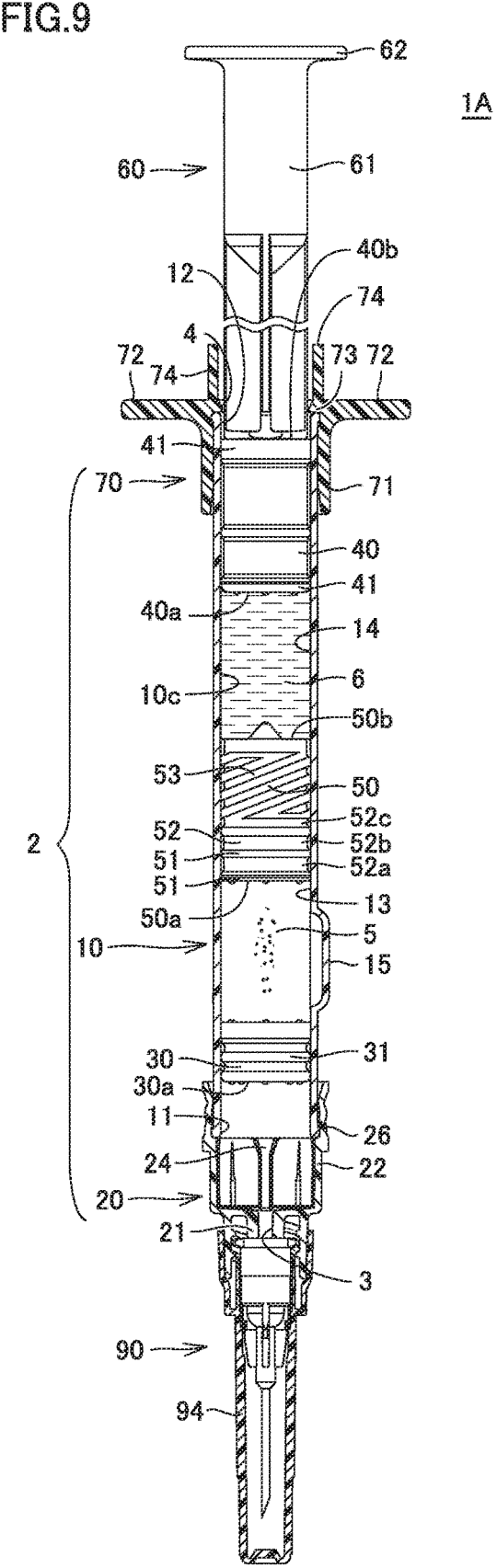
FIG. 9 is a schematic cross-sectional view of a pre-filled syringe according to the second embodiment of the present invention.

FIG. 9 is a schematic cross-sectional view of a pre-filled syringe according to the present embodiment. Referring to FIG. 9, a pre-filled syringe 1A according to the present embodiment will be hereinafter described.

As shown in FIG. 9, as compared with pre-filled syringe 1 according to the first embodiment, pre-filled syringe 1A according to the present embodiment is different in configurations of plunger 60 and flange portion 70, but almost identical in other configurations.

Plunger 60 employed in the present embodiment is configured such that rod portion 61 is not provided with a protruding portion according to the first embodiment. Also, flange portion 70 employed in the present embodiment further includes a protruding portion 74.

Protruding portion 74 is provided to protrude toward the outside in the axial direction of cylindrical container 2 so as to be located in a portion of flange portion 70 that faces diameter increasing portion 62 of plunger 60. Protruding portion 74 is configured so as not to interfere with rod portion 61.

In pre-filled syringe 1A according to the present embodiment, the operation of mixing medical drug 5 and liquid drug 6 to prepare and discharge liquid mixture L is performed basically according to the operation performed in the case of pre-filled syringe 1 in the first embodiment, and therefore, description thereof will not be repeated.

FIG. 10 is a schematic cross-sectional view showing the state where a liquid mixture is discharged from the pre-filled syringe shown in FIG. 9. Referring to FIG. 10, an explanation will be hereinafter given with regard to the state where liquid mixture L is discharged from pre-filled syringe 1A.

As shown in FIG. 10, in the state where the liquid mixture is discharged from pre-filled syringe 1A, diameter increasing portion 62 of plunger 60 comes in contact with protruding portion 74 of flange portion 70 on the rear end side of cylindrical container 2. Accordingly, front end-side gasket 30 is pushed in by intermediate gasket 50, thereby limiting movement of plunger 60 at the position where nozzle portion 20 does not fall off from cylindrical portion 10. Furthermore, movement of plunger 60 is limited such that tail end 40b of rear end-side gasket 40 located closer to plunger 60 does not reach bypass portion 15.

In this way, in pre-filled syringe 1A according to the present embodiment, diameter increasing portion 62 and protruding portion 74 each function as a movement limiting mechanism for limiting movement of plunger 60. Consequently, the present embodiment can also achieve almost the same effects as those achieved in the first embodiment.

Third Embodiment

Figure 11:
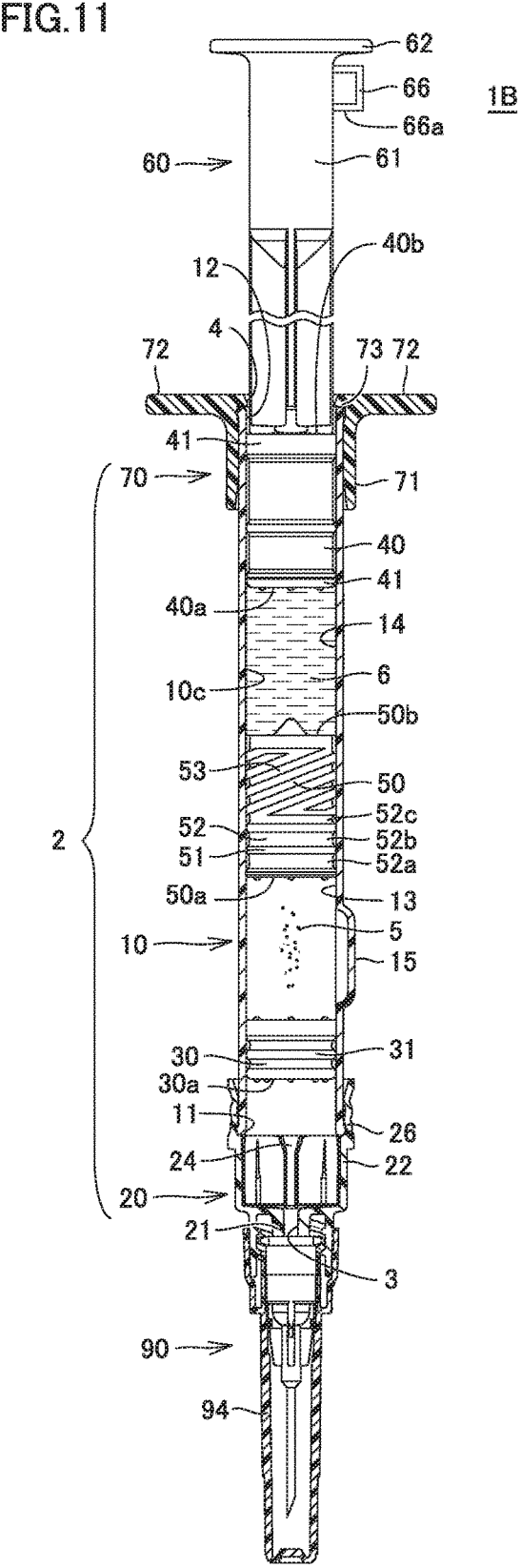
FIG. 11 is a schematic cross-sectional view of a pre-filled syringe according to the third embodiment of the present invention.

FIG. 11 is a schematic cross-sectional view of a pre-filled syringe according to the present embodiment. Referring to FIG. 11, a pre-filled syringe 1B according to the present embodiment will be hereinafter described.

As shown in FIG. 11, as compared with pre-filled syringe 1 according to the first embodiment, pre-filled syringe 1B according to the present embodiment is different in configuration of plunger 60, but almost identical in other configurations.

Plunger 60 employed in the present embodiment is configured such that a pin 66 is inserted into an insertion hole provided in rod portion 61. A portion 66a of pin 66 that is exposed from rod portion 61 functions as protruding portion 63 according to the first embodiment.

In pre-filled syringe 1B according to the present embodiment, the operation of mixing medical drug 5 and liquid drug 6 to prepare and discharge a liquid mixture is performed basically according to the operation performed in the case of pre-filled syringe 1 in the first embodiment, and therefore, description thereof will not be repeated.

FIG. 12 is a schematic cross-sectional view showing the state where a liquid mixture is discharged from the pre-filled syringe shown in FIG. 11. Referring to FIG. 12, an explanation will be hereinafter given with regard to the state where liquid mixture L is discharged from the pre-filled syringe.

As shown in FIG. 12, in the state where liquid mixture L is discharged from the pre-filled syringe, portion 66a of pin 66 exposed from rod portion 61 comes in contact with flange portion 70 on the rear end side of cylindrical container 2. Accordingly, front end-side gasket 30 is pushed in by intermediate gasket 50, thereby limiting movement of plunger 60 at the position where nozzle portion 20 does not fall off from cylindrical portion 10. Furthermore, movement of plunger 60 is limited such that tail end 40b of rear end-side gasket 40 located closer to plunger 60 does not reach bypass portion 15.

In this way, in pre-filled syringe 1B according to the present embodiment, flange portion 70 and portion 66a, which is included in pin 66 inserted into rod portion 61 and exposed from rod portion 61, function as a movement limiting mechanism for limiting movement of plunger 60. Consequently, the present embodiment can also achieve almost the same effects as those achieved in the first embodiment.

Fourth Embodiment

Figure 13:
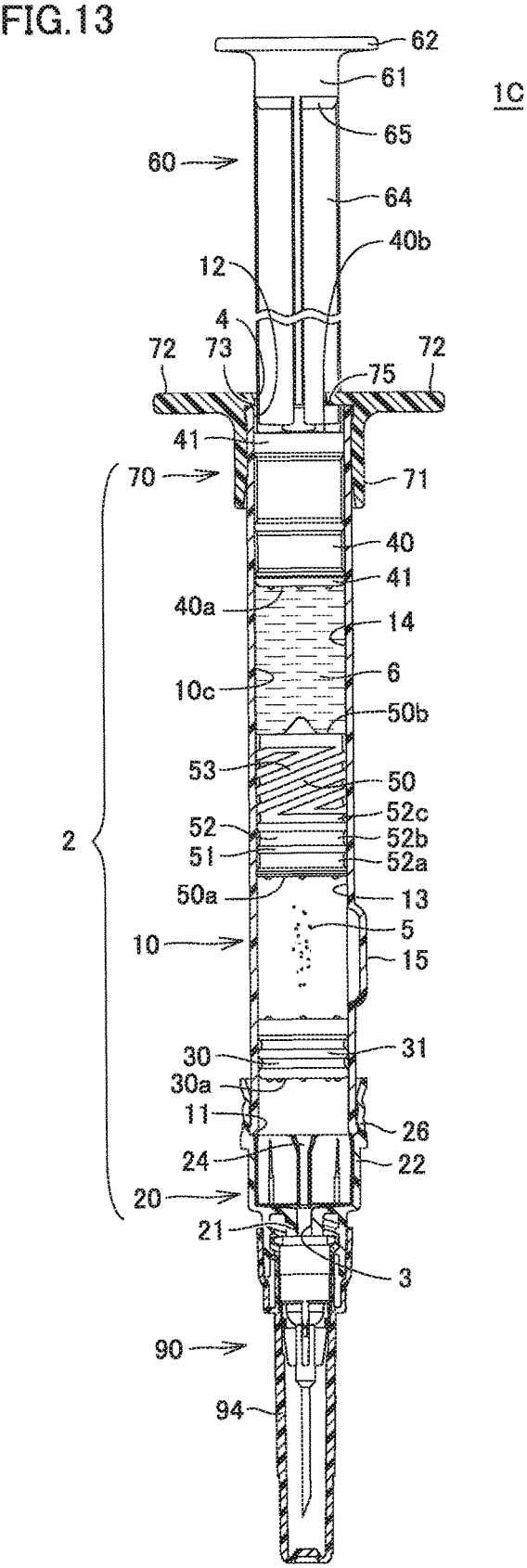
FIG. 13 is a schematic cross-sectional view of a pre-filled syringe according to the fourth embodiment of the present invention.
Figure 14:
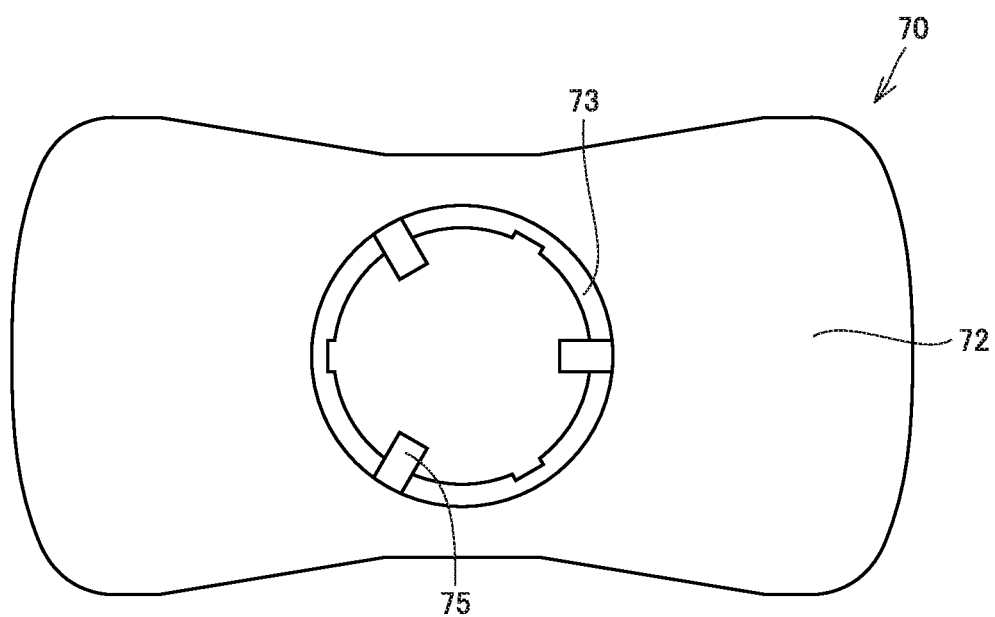
FIG. 14 is a plan view of a flange portion shown in FIG. 13.

FIG. 13 is a schematic cross-sectional view of a pre-filled syringe according to the present embodiment. FIG. 14 is a plan view of a flange portion shown in FIG. 13. Referring to FIGS. 13 and 14, a pre-filled syringe 1C according to the present embodiment will be hereinafter described.

As shown in FIG. 13, as compared with pre-filled syringe 1 according to the first embodiment, pre-filled syringe 1C according to the present embodiment is different in configurations of plunger 60 and flange portion 70 but almost identical in other configurations.

Plunger 60 used in the present embodiment is configured to have a cutout groove portion 64. Cutout groove portion 64 is formed in a groove shape depressed in the radially inward direction of rod portion 61 and extending from the vicinity of diameter increasing portion 62 to the joint portion between rod portion 61 and rear end-side gasket 40. Cutout groove portion 64 has a rear end provided with an end face 65.

As shown in FIGS. 13 and 14, flange portion 70 used in the present embodiment is configured to further include a protruding portion 75. Protruding portion 75 is provided so as to protrude from engagement portion 73 to the inside and located at a position corresponding to cutout groove portion 64.

FIG. 15 is a schematic cross-sectional view showing the state where a liquid mixture is discharged from the pre-filled syringe shown in FIG. 13. Referring to FIG. 15, an explanation will be hereinafter given with regard to the state where a liquid mixture is discharged from the pre-filled syringe.

As shown in FIG. 15, in the state where the liquid mixture is discharged from the pre-filled syringe, end face 65 of plunger 60 comes in contact with protruding portion 75 of flange portion 70 on the rear end side of cylindrical container 2. Accordingly, front end-side gasket 30 is pushed in by intermediate gasket 50, thereby limiting movement of plunger 60 at the position where nozzle portion 20 does not fall off from cylindrical portion 10. Furthermore, movement of plunger 60 is limited such that tail end 40b of rear end-side gasket 40 located closer to plunger 60 does not reach bypass portion 15.

In this way, in pre-filled syringe 1C according to the present embodiment, end face 65 and protruding portion 75 each function as a movement limiting mechanism for limiting movement of plunger 60. Consequently, the present embodiment can also achieve almost the same effects as those achieved in the first embodiment.

Although explanations have been given in the above-described first to fourth embodiments by way of example with regard to the case where cylindrical portion 10 and nozzle portion 20 are separately formed, the present invention is not limited thereto, but cylindrical portion 10 and nozzle portion 20 may be integrally formed. Similarly, cylindrical portion 10 and flange portion 70 may also be integrally formed.

Although the embodiments of the present invention have been described as above, it should be understood that the embodiments disclosed herein are illustrative and non-restrictive in every respect. The scope of the present invention is defined by the terms of the claims, and is intended to include any modifications within the meaning and scope equivalent to the terms of the claims.

REFERENCE SIGNS LIST 1, 1A, 1B, 1C pre-filled syringe, 2 cylindrical container, 3 discharge path, 4 opening, 5 medical drug, 6 liquid drug, 10 cylindrical portion, 11, 12 opening, 13 front chamber, 14 rear chamber, 15, 50 bypass portion, 20 nozzle portion, 21 discharge portion, 22 housing portion, 22a inner circumferential surface, 22b bottom surface, 24 flow passage portion, 24a narrow-width portion, 24b wide-width portion, 25 insertion portion, 26 attachment portion, 30 front end-side gasket, 30a front end, 30b, 30c circumferential surface, 40 rear end-side gasket, 40a fore end, 40b tail end, 41 annular rib, 50 intermediate gasket, 50a fore end, 50b rear end, 51 annular rib, 52, 52c annular groove portion, 53 spiral groove portion, 60 plunger, 61 rod portion, 62 diameter increasing portion, 63 protruding portion, 64 groove portion, 65 end face, 66 pin, 70 flange portion, 71 cylindrical portion, 72 flange portion, 73 engagement portion, 73a inclined surface, 74 protruding portion, 75 protruding portion, 90 injection needle unit, 91 base body, 92 puncture needle, 93 hollow passage, 94 protector.

The invention claimed is:

1. A pre-filled syringe comprising:
a cylindrical container having a front end provided with a discharge path and a rear end provided with an opening;
a front end-side gasket provided at a position closer to the front end of the cylindrical container so as to partition a space inside the cylindrical container, the front end-side gasket being freely slidable inside the cylindrical container;
a rear end-side gasket provided at a position closer to the rear end of the cylindrical container so as to partition the space inside the cylindrical container, the rear end-side gasket being freely slidable inside the cylindrical container;
an intermediate gasket provided inside the cylindrical container so as to partition, into a front chamber and a rear chamber, a portion of the space inside the cylindrical container that is located between the front end-side gasket and the rear end-side gasket, the intermediate gasket being freely slidable inside the cylindrical container;
a plunger, a part of which being inserted through the opening into the cylindrical container such that the plunger is connected to the rear end-side gasket, thereby allowing the rear end-side gasket to be pushed toward the front end of the cylindrical container, wherein the plunger includes a rod portion and an increased diameter portion, the increased diameter portion is located at an end of the plunger;
a medical drug contained in the front chamber; and
a liquid drug contained in the rear chamber, wherein:
the cylindrical container has a bypass portion protruding in a radially outward direction;
the intermediate gasket has an outer circumferential surface provided with a groove portion that faces the bypass portion in a state where the intermediate gasket is disposed to face the bypass portion,
in a state Where the plunger is not pushed in, the bypass portion faces the front chamber and does not face the groove portion, thereby allowing the front chamber and the rear chamber to be maintained in a liquid-tight state by the intermediate gasket, and the front chamber does not communicate with the discharge path, thereby allowing the front chamber and the discharge path to be maintained in a liquid-tight state by the front end-side gasket,
in a state where the plunger is pushed in, the rear end-side gasket, the intermediate gasket and the front end-side gasket move toward the front end of the cylindrical container, to cause the bypass portion to face the groove portion, thereby allowing communication between the front chamber and the rear chamber through the bypass portion and the groove portion, to mix the medical drug and the liquid drug so as to prepare a liquid mixture, and allowing communication between the front chamber and the discharge path, to cause the liquid mixture to be discharged through the discharge path to outside,
the cylindrical container includes a cylindrical portion housing the front end-side gasket, the intermediate gasket and the rear end-side gasket in the state where the plunger is not pushed in and a nozzle portion having the discharge path and attached to a fore end of the cylindrical portion,
the nozzle portion includes a housing portion located adjacent to the fore end of the cylindrical portion and being capable of housing the front end-side gasket in the state where the plunger is pushed in, and
the pre-filled syringe further comprises a movement limiting mechanism, separate from the intermediate gasket, for limiting movement of the plunger such that a tail end of the rear end-side gasket located closer to the plunger is prevented from reaching the bypass portion in the state where the plunger is pushed in to a position where the front end-side gasket is housed in the housing portion with the intermediate gasket in contact with the front end-side gasket, and
the intermediate gasket comprises:
a plurality of annular groove portions formed in a circumferential direction;
annular ribs, each annular rib being, provided between adjacent annular groove portions; and
a spiral groove portion formed in a spiral shape,
wherein the movement limiting mechanism includes a protruding portion protruding radially outward from the rod portion of the plunger and extending only partially around a circumference of the rod portion of the plunges,
wherein the protruding portion of the rod portion of the plunger is located approximate to a base of the increased diameter portion,
wherein the rod portion of the plunger is connected to the rear end-side gasket and extends in an axial direction of the cylindrical container such that a part of the rod portion of the plunger is located outside the cylindrical container,
wherein the rod portion of the plunger includes a cylinder portion provided at a rear end side of the rod portion of the plunger,
wherein the increased diameter portion is located at an end of the cylinder portion, and
wherein the protruding portion is provided on an outer peripheral surface of the cylinder portion.

2. The pre-filled syringe according to claim 1, wherein:
the protruding portion is located outside the cylindrical container in the state where the plunger is not pushed in, and
in the state where the plunger is pushed in, the protruding portion comes in contact with the cylindrical container, thereby limiting movement of the plunger.

3. The pre-filled syringe according to claim 1, wherein
the nozzle portion includes a discharge portion located closer to a front end of the nozzle portion and communicating with the housing portion,
the discharge path is defined by the housing portion and the discharge portion,
in the state where the plunger is pushed in, the discharge portion and the front chamber communicate with each other through a space between the housing portion and a circumferential surface of the front end-side gasket moved from the cylindrical portion to the housing portion, thereby discharging the liquid mixture through the discharge path to outside, and
when the plunger is pushed in, the front end-side gasket is pushed in by the intermediate gasket, thereby limiting movement of the plunger at a position where the nozzle portion does not fall off from the cylindrical portion.

4. The pre-filled syringe according to claim 1, wherein the protruding portion has a contact face coming in contact with the rear end of the cylindrical container in the state where the plunger is pushed in, and
wherein the contact face of the protruding portion extends in the circumferential direction along a part of the outer peripheral surface of the cylinder portion.

* * * * *